(12) United States Patent
Suzuki et al.

(10) Patent No.: US 9,492,371 B2
(45) Date of Patent: *Nov. 15, 2016

(54) COSMETIC COMPOSITION

(71) Applicant: KAO CORPORATION, Chuo-ku (JP)

(72) Inventors: Hirohisa Suzuki, Funabashi (JP);
Yoshiaki Matsui, Izumisano (JP);
Takashi Kodate, Wakayama (JP)

(73) Assignee: KAO CORPORATION, Chuo-ku (JP)

( * ) Notice: Subject to any disclaimer, the term of this patent is extended or adjusted under 35 U.S.C. 154(b) by 110 days.

This patent is subject to a terminal disclaimer.

(21) Appl. No.: 14/381,351

(22) PCT Filed: Feb. 25, 2013

(86) PCT No.: PCT/JP2013/054798
§ 371 (c)(1),
(2) Date: Aug. 27, 2014

(87) PCT Pub. No.: WO2013/129329
PCT Pub. Date: Sep. 6, 2013

(65) Prior Publication Data
US 2015/0030647 A1   Jan. 29, 2015

(30) Foreign Application Priority Data
Feb. 28, 2012   (JP) .................. 2012-041703

(51) Int. Cl.
*A61K 8/02* (2006.01)
*A61K 8/27* (2006.01)
(Continued)

(52) U.S. Cl.
CPC .............. *A61K 8/897* (2013.01); *A61K 8/022* (2013.01); *A61K 8/0241* (2013.01); *A61K 8/064* (2013.01); *A61K 8/19* (2013.01); *A61K 8/25* (2013.01); *A61K 8/26* (2013.01); *A61K 8/27* (2013.01); *A61K 8/29* (2013.01); *A61K 8/37* (2013.01); *A61K 8/70* (2013.01); *A61K 8/88* (2013.01); *A61Q 1/00* (2013.01); *A61Q 1/02* (2013.01); *A61Q 17/04* (2013.01); *A61K 2800/52* (2013.01); *A61K 2800/612* (2013.01); *A61K 2800/614* (2013.01); *A61Q 1/04* (2013.01); *A61Q 1/06* (2013.01); *A61Q 1/08* (2013.01)

(58) Field of Classification Search
None
See application file for complete search history.

(56) References Cited

U.S. PATENT DOCUMENTS 5,548,054 A   8/1996 Okada et al.
5,700,898 A   12/1997 Okada et al.
(Continued)

FOREIGN PATENT DOCUMENTS

JP   2-295913    12/1990
JP   6-184312    7/1994
(Continued)

OTHER PUBLICATIONS

Extended Search Report issued Oct. 30, 2015 in European Patent Application No. 13755131.3.
(Continued)

*Primary Examiner* — Lakshmi Channavajjala
(74) *Attorney, Agent, or Firm* — Oblon, McClelland, Maier & Neustadt, L.L.P.

(57) ABSTRACT

A cosmetic composition, comprising the following components (A), (B), (C), and (D):

(A) from 0.01 to 48 % by mass of a fluorine-modified silicone having a polysiloxane unit represented by the following formulae (1) and (2):

wherein, Rf represents a linear or branched perfluoroalkyl group having 6 carbon atoms; $R^1$, $R^2$, and $R^3$ are the same or different and each represent a linear or branched hydrocarbon group having 1 to 6 carbon atoms; m represents a number of 2 to 6; n represents a number of 1 to 6; p represents a number of 3 to 50; s represents a number of 1 to 5; and a ratio between p and s satisfies $0.66 \leq p/(p+s) \leq 0.9$, (B) from 0.01 to 40 % by mass of a powder having been subjected to a surface treatment with tridecafluoro octyltriethoxysilane, (C) from 0.01 to 20% by mass of a fine zinc oxide particle having a specific surface area of 10 to 100 m²/g, with the proviso that the component (B) is excluded from the component (C), and (D) octyl para-methoxycinnamate, wherein, a mass ratio of the component (A) to the component (D), (A)/(D) is from 0.5 to 10.

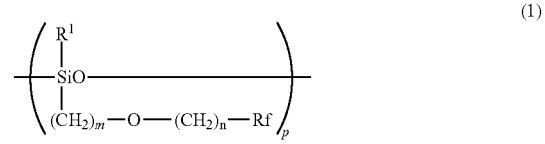

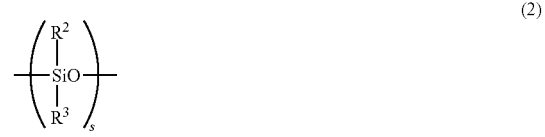

24 Claims, No Drawings

(51) Int. Cl.
*A61K 8/25* (2006.01)
*A61K 8/897* (2006.01)
*A61K 8/37* (2006.01)
*A61Q 17/04* (2006.01)
*A61K 8/06* (2006.01)
*A61K 8/26* (2006.01)
*A61K 8/29* (2006.01)
*A61Q 1/00* (2006.01)
*A61Q 1/02* (2006.01)
*A61K 8/70* (2006.01)
*A61K 8/88* (2006.01)
*A61K 8/19* (2006.01)
*A61Q 1/04* (2006.01)
*A61Q 1/06* (2006.01)
*A61Q 1/08* (2006.01)

(56) References Cited

U.S. PATENT DOCUMENTS 5,976,518 A   11/1999   Okada et al.
6,018,082 A   1/2000    Okada et al.
2010/0269733 A1*  10/2010   Kremitzl .............. B82Y 30/00
                                                               106/404

FOREIGN PATENT DOCUMENTS

| JP | 7-277914 | 10/1995 |
| JP | 7-330544 | 12/1995 |
| JP | 9-249518 | 9/1997 |
| JP | 10-139623 | 5/1998 |
| JP | 2008-143821 | 6/2008 |
| JP | 2008-143837 | 6/2008 |
| JP | 2009-35511 | 2/2009 |
| JP | 2012-12302 | 1/2012 |

OTHER PUBLICATIONS

International Search Report issued May 28, 2013, in PCT/JP2013/054798, filed Feb. 25, 2013.
International Preliminary Report on Patentability and Written Opinion issued Sep. 12, 2014 in PCT/JP2013/054798 (English translation only).
U.S. Appl. No. 14/380,608, filed Aug. 22, 2014, Suzuki, et al.

* cited by examiner

COSMETIC COMPOSITION

CROSS REFERENCE TO RELATED APPLICATION

This application is a 371 of PCT/JP2013/054798, filed on Feb. 25, 2013, and claims priority to Japanese Patent Application No. 2012-041703, filed on Feb. 28, 2012.

FIELD OF THE INVENTION

The present invention relates to a cosmetic composition.

BACKGROUND OF THE INVENTION

When only conventional powders are incorporated into cosmetic compositions, the powders are markedly wetted with sweat, sebum, and the like on the skin, eventually presenting a mirror-like appearance. This makes it difficult to maintain the makeup finish immediately after application. In light of this, with the aim of improving durability of makeup and preventing makeup deterioration, cosmetic compositions containing various water and oil repellent compounds have been studied.

For example, Patent Literature 1 describes a cosmetic composition containing a specific fluorine-modified silicone derivative and Patent Literature 2 describes a cosmetic composition containing a fluorine-modified silicone and a fine zinc oxide particle.

It has been proposed that these cosmetic compositions strongly prevent makeup deterioration and have excellent durability of makeup.

CITATION LIST

Patent Literature

[Patent Literature 1] JP-A-6-184312
[Patent Literature 2] JP-A-7-277914

SUMMARY OF THE INVENTION

The present invention relates to a cosmetic composition, comprising the following components (A), (B), (C), and (D):
(A) from 0.01 to 48% by mass of a fluorine-modified silicone having a polysiloxane unit represented by the following formulae (1) and (2):

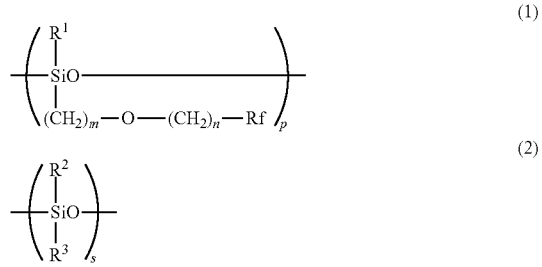

wherein, Rf represents a linear or branched perfluoroalkyl group having 6 carbon atoms; $R^1$, $R^2$, and $R^3$ are the same or different and each represent a linear or branched hydrocarbon group having 1 to 6 carbon atoms; m represents a number of from 2 to 6; n represents a number of from 1 to 6; p represents a number of from 3 to 50; s represents a number of from 1 to 5; and a ratio between p and s satisfies $0.66 \leq p/(p+s) \leq 0.9$,
(B) from 0.01 to 40% by mass of a powder having been subjected to a surface treatment with tridecafluoro octyltriethoxysilane,
(C) from 0.01 to 20% by mass of a fine zinc oxide particle having a specific surface area of from 10 to 100 m²/g, with the proviso that the component (B) is excluded from the component (C), and
(D) octyl para-methoxycinnamate,
wherein, a mass ratio of the component (A) to the component (D), (A)/(D), is from 0.5 to 10.

DETAILED DESCRIPTION OF THE INVENTION

Various ultraviolet protective agents are incorporated into cosmetic compositions. Among ultraviolet protective agents, octyl para-methoxycinnamate is widely used since it has an excellent ultraviolet protective effect but is less irritating to the skin, and thus is highly safe. However, it is difficult to stably incorporate an oil agent such as a fluorine-modified silicone and a volatile silicone and octyl para-methoxycinnamate into cosmetic compositions. Particularly, their low temperature stability was found to be a problem. Further, another problem was found that cosmetic compositions with insufficient adhesion to the skin have poor skin compatibility.

The present invention relates to a highly safe cosmetic composition with excellent adhesion to the skin.

The present inventors have found that a cosmetic composition which solves the aforementioned problems can be obtained by using a combination of a specific fluorine-modified silicone, a powder treated with a fluorine compound, a fine zinc oxide particle, and octyl para-methoxycinnamate in a specific ratio.

The cosmetic composition of the present invention has excellent stability, particularly low temperature stability, and upon application, it exerts excellent adhesion and attachment to the skin.

The fluorine-modified silicone of the component (A) used in the present invention has a polysiloxane unit represented by the above formulae (1) and (2).

In the formulae, examples of the hydrocarbon groups represented by $R^1$, $R^2$, and $R^3$ include a linear alkyl group such as a methyl group, an ethyl group, a propyl group, a butyl group, a pentyl group, and a hexyl group; a branched alkyl group such as an isopropyl group, a sec-butyl group, a tert-butyl group, a neopentyl group, and a 1-ethylpropyl group; and a cyclic alkyl group such as cyclopentyl and cyclohexyl.

Also, m represents a number of from 2 to 6, preferably from 2 to 5, more preferably 3. Also, n represents a number of from 1 to 6, preferably from 1 to 4, more preferably 2.

Also, p represents a number of from 3 to 50, preferably from 3 to 10, more preferably from 3 to 6. Also, s represents a number of from 1 to 5, preferably from 1 to 3, more preferably 1.

Also, in order to achieve excellent stability, good skin compatibility, excellent durability of makeup, and a moist feeling upon application, the ratio between p and s, namely, the modification rate of the polysiloxane unit p represented by the formula (1) to the sum of the polysiloxane units p+s represented by the formulae (1) and (2), satisfies $0.66 \leq p/(p+s) \leq 0.9$, preferably $0.75 \leq p/(p+s) \leq 0.83$.

The fluorine-modified silicone of the component (A) can be produced in accordance with, for example, the method described in JP-A-6-184312.

As the component (A), a fluorine-modified silicone represented by the following formula (3) is preferable.

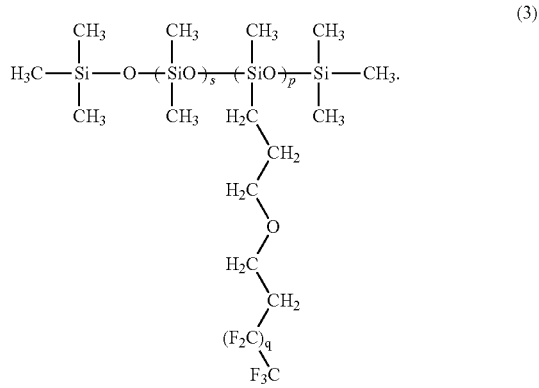

wherein, p and s have the same meaning as above and q represent a number of 5.

The component (A) can be used singly or in combination of two or more thereof, and in order to achieve excellent stability and feeling upon application as well as durability of makeup, the content thereof is, relative to the whole cosmetic composition, 0.01% by mass or more, preferably 0.1% by mass or more, more preferably 1% by mass or more, even more preferably 4% by mass or more, and 48% by mass or less, preferably 30% by mass or less, more preferably 20% by mass or less, even more preferably 15% by mass or less. Further, the content of the component (A) is from 0.01 to 48% by mass, preferably from 0.1 to 30% by mass, more preferably from 1 to 20% by mass, and even more preferably from 4 to 15% by mass of the total composition.

The powder of the component (B) used in the present invention is a powder having been subjected to a surface treatment with tridecafluoro octyltriethoxysilane represented by the following formula.

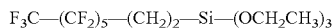
$F_3C—(CF_2)_5—(CH_2)_2—Si—(OCH_2CH_3)_3$

Excellent stability, good skin compatibility, and a moist feeling upon application can be obtained by using a powder having been subjected to a surface treatment with tridecafluoro octyltriethoxysilane of fluorine compounds used for the surface treatment of the powder. As tridecafluoro octyltriethoxysilane, FHS sold by Daito Kasei Kogyo Co., Ltd. is preferable.

The powder to be treated is not particularly limited as long as it is an extender pigment or color pigment used in conventional cosmetic compositions. Examples thereof include an inorganic powder such as silicic acid, anhydrous silicic acid, magnesium silicate, talc, sericite, mica, kaolin, red iron oxide, clay, bentonite, titanium-coated mica, bismuth oxychloride, zirconium oxide, magnesium oxide, titanium oxide, zinc oxide, aluminum oxide, calcium sulfate, barium sulfate, magnesium sulfate, calcium carbonate, magnesium carbonate, iron oxide, ultramarine, chromium oxide, chromium hydroxide, calamine, carbon black, and a complex of these materials; an organic powder such as polyamide, polyester, polypropylene, polystyrene, polyurethane, vinyl resin, urea resin, phenolic resin, fluororesin, silicone resin, acrylic resin, melamine resin, epoxy resin, polycarbonate resin, a divinylbenzene-styrene copolymer, silk powder, cellulose, long-chain alkyl phosphate metal salt, N-mono long-chain alkyl acyl basic amino acid, and a complex of these materials; and further, a complex powder of the aforementioned inorganic powder and organic powder. Among these materials, titanium oxide, red iron oxide, yellow iron oxide, black iron oxide, mica, titanium-coated mica, nylon powder, silica, talc, and sericite are preferable.

As a method of surface treatment of a powder with tridecafluoro octyltriethoxysilane, for example, the following methods can be performed, which are: a method comprising dropping or adding tridecafluoro octyltriethoxysilane to a powder and mixing them in a mixer, followed by heat treatment and, if necessary, crushing; and a method comprising dissolving or dispersing tridecafluoro octyltriethoxysilane in an organic solvent and then mixing the resulting organic solvent solution with a powder, followed by removing the organic solvent, and then crushing the product obtained after drying.

Among those methods, the following method is given as a preferred method: a production method comprising dissolving or dispersing tridecafluoro octyltriethoxysilane in an organic solvent and, while mixing the resulting organic solvent with a powder in a mixer, removing the organic solvent by heating the mixer under reduced pressure, followed by heat treatment and crushing as needed. Suitable examples of the organic solvent used in this method include a polar organic solvent represented by methanol, ethanol, isopropyl alcohol, isobutanol, acetone, ethyl acetate, butyl acetate, methyl ethyl ketone, dichloromethane, and chloroform and a hydrocarbon organic solvent such as normal hexane, toluene, and xylene.

The amount of tridecafluoro octyltriethoxysilane used in the treatment varies depending on the powder; however, relative to the mass of the powder of the component (B), the amount of tridecafluoro octyltriethoxysilane used in the treatment is preferably 0.05% by mass or more, more preferably 0.1% by mass or more, preferably 50% by mass or less, more preferably 20% by mass or less. Also, relative to the mass of the powder of the component (B), the amount of tridecafluoro octyltriethoxysilane used in the treatment is preferably from 0.05 to 50% by mass, more preferably from 0.1 to 20% by mass. It is preferable that the amount of tridecafluoro octyltriethoxysilane used in the treatment be in the above range so that the resulting cosmetic composition exerts sufficient water and oil repellent properties and achieves favorable feeling to the touch and fluidity.

In consideration of powderiness during application and makeup finish, the average particle diameter of the component (B) is preferably from 0.1 to 20 μm, more preferably from 0.1 to 10 μm.

It should be noted that in the present invention, the particle diameter of the component (B) is measured by electron microscopic observation or by the laser diffraction/scattering method using a particle size distribution measuring device. Specifically, in the case of the laser diffraction/scattering method, the particle diameter of the component (B) is measured by a laser diffraction scattering particle size distribution measuring device (for example, Model LA-920, the product of Horiba, Ltd.), using ethanol as a dispersion medium.

The component (B) can be used singly or in combination of two or more thereof, and in consideration of makeup finish and stability, the content thereof is, relative to the whole cosmetic composition, 0.01% by mass or more, preferably 0.1% by mass or more, more preferably 1% by mass or more, even more preferably 5% by mass or more, and 40% by mass or less, preferably 30% by mass or less, more preferably 25% by mass or less, and even more preferably 20% by mass or less. Also, the content of the component (B) is from 0.01 to 40% by mass, preferably from 0.1 to 30% by mass, more preferably from 1 to 25% by mass, and even more preferably from 5 to 20% by mass of the total composition.

In consideration of the feeling upon application and durability of makeup, in the present invention, the mass ratio of component (A) to component (B), (A)/(B), is preferably 0.01 or more, more preferably 0.1 or more, even more preferably 0.2 or more, and preferably 50 or less, more preferably 20 or less, even more preferably 10 or less, and further preferably 2 or less. Also, the mass ratio of component (A) to component (B), (A)/(B), is preferably from 0.01 to 50, more preferably from 0.1 to 20, even more preferably from 0.1 to 10, and further preferably from 0.2 to 2.

The fine zinc oxide particle of the component (C) used in the present invention is a fine zinc oxide particle having a specific surface area of from 10 to 100 m²/g, preferably from 15 to 95 m²/g. Excellent durability of makeup and favorable feeling upon application can be obtained by using a fine zinc oxide particle having such a specific surface area.

It should be noted that the component (C) used in the present invention excludes the component (B), meaning that the component (C) does not include the component (B).

Although the fine zinc oxide particle of the component (C) can be directly used, it is also possible to use a fine zinc oxide particle which has been subjected to a water and/or an oil repellent treatment with silicone, metal soap, lecithin, N-acylamino acid, a fluorine compound, and the like, as needed. In order to prevent makeup deterioration and improve the dispersibility of fine zinc oxide particles in the cosmetic composition, a silicone-treated fine zinc oxide particle is preferable, and it is more preferable to perform a silicone treatment using methyl hydrogen polysiloxane. These treatments can be performed in accordance with conventional methods.

The component (C) can be used singly or in combination of two or more thereof, and in consideration of the durability of makeup, the content thereof is, relative to the whole cosmetic composition, 0.01% by mass or more, preferably 0.1% by mass or more, more preferably 1% by mass or more, and 20% by mass or less, preferably 10% by mass or less, and more preferably 8% by mass or less. Also, the content of the component (C) is from 0.01 to 20% by mass, preferably from 0.1 to 10% by mass, and more preferably from 1 to 8% by mass of the total composition.

In consideration of the durability of makeup, in the present invention, the mass ratio of the component (A) to the component (C), (A)/(C), is preferably 0.1 or more, more preferably 0.9 or more, and preferably 10 or less, more preferably 7 or less. Also, the mass ratio of the component (A) to the component (C), (A)/(C), is preferably from 0.1 to 10, more preferably from 0.9 to 7.

In consideration of protection against ultraviolet rays, the content of octyl para-methoxycinnamate of the component (D) used in the present invention is, relative to the whole cosmetic composition, preferably 0.1% by mass or more, more preferably 1% by mass or more, and preferably 15% by mass or less, more preferably 10% by mass or less. Also, the content of the component (D) is preferably from 0.1 to 15% by mass, more preferably from 1 to 10% by mass of the total composition.

In the present invention, the mass ratio of the component (A) to the component (D), (A)/(D), is from 0.5 to 10. In consideration of stability and protection against ultraviolet rays, the mass ratio of the component (A) to the component (D) is preferably 1 or more, more preferably 1.3 or more, and preferably 5 or less, more preferably 4 or less. Also, the mass ratio of the component (A) to the component (D), (A)/(D), is preferably from 1 to 5, more preferably from 1.3 to 4.

The cosmetic composition of the present invention can further comprise (E) an organopolysiloxane in which poly(N-acylalkyleneimine) segments are bound to at least two silicon atoms of an organopolysiloxane segment constituting the main chain via alkylene groups each having a hetero atom, the poly(N-acylalkyleneimine) segments comprising a repeating unit represented by the following formula (4):

wherein, $R^4$ represents a hydrogen atom or an alkyl group having 1 to 3 carbon atoms and t represents 2 or 3, wherein, the number average molecular weight of the poly(N-acylalkyleneimine) segment is from 500 to 4000; the mass ratio of (a) the organopolysiloxane segment constituting the main chain to (b) the poly(N-acylalkyleneimine) segment, (a/b), is from 80/20 to 95/5; the weight average molecular weight of the organopolysiloxane segment between adjacent poly(N-acylalkyleneimine) segments is from 10000 to 40000; and the weight average molecular weight of the organopolysiloxane segment constituting the main chain is from 50000 to 150000. Thus, higher stability can be achieved.

At least two poly(N-acylalkyleneimine) segments are bound to an arbitrary silicon atom constituting the aforementioned organopolysiloxane segment via an alkylene group having a hetero atom. Further, it is preferable that poly(N-acylalkyleneimine) segments be bound to one or more silicon atoms other than those at both ends of the aforementioned organopolysiloxane segment via the aforementioned alkylene group(s), and it is more preferable that poly(N-acylalkyleneimine) segments be bound to two or more silicon atoms other than those at both ends via the aforementioned alkylene groups. That is, the organopolysiloxane of the component (E) is a graft polymer containing, as a side chain, at least two or more poly(N-acylalkyleneimine) segments comprising a repeating unit represented by the above formula (4).

The alkylene group having a hetero atom functions as a linking group of the poly(N-acylalkyleneimine) segment. Examples of the alkylene group include an alkylene group having 2 to 20 carbon atoms, which contains 1 to 3 nitrogen atoms, oxygen atoms, or sulfur atoms. Among them, a group represented by any one of the following formulae (i) to (vii) is preferable, and a group represented by the following formula (i) or (ii) is more preferable, and a group represented by the following formula (i) is even more preferable. It should be noted that, in the formulae, $An^-$ represents a counterion of a quaternary ammonium salt, and examples thereof include an ethyl sulfate ion, a methyl sulfate ion, a chloride ion, an iodide ion, a sulfate ion, a p-toluene sulfonate ion, and a perchlorate ion.

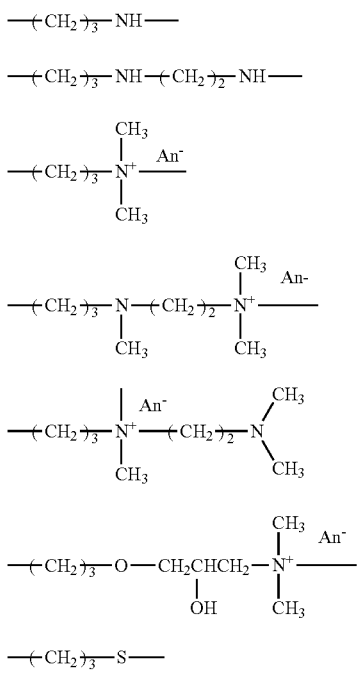

(i) —(CH₂)₃—NH—

(ii) —(CH₂)₃—NH—(CH₂)₂—NH—

(iii) 
$$-(CH_2)_3-\overset{CH_3}{\underset{CH_3}{\overset{|}{N^+}}}-\;An^-$$

(iv) 
$$-(CH_2)_3-\overset{CH_3}{\underset{CH_3}{\overset{|}{N}}}-(CH_2)_2-\overset{CH_3}{\underset{CH_3}{\overset{|}{N^+}}}-\;An^-$$

(v) 
$$-(CH_2)_3-\overset{An^-}{\overset{|}{N^+}}-(CH_2)_2-N\overset{CH_3}{\underset{CH_3}{\diagdown}}$$

(vi) 
$$-(CH_2)_3-O-CH_2CHCH_2-\overset{CH_3}{\underset{CH_3}{\overset{|}{N^+}}}-\;An^-\\\;\;\;\;\;\;\;\;\;\;\;\;\;\;\;\;\;\;\;\;\;\;\;\;\;OH$$

(vii) —(CH₂)₃—S—

In the N-acylalkyleneimine unit constituting the poly(N-acylalkyleneimine) segment, examples of the alkyl group having 1 to 3 carbon atoms as $R^4$ in the formula (4) include a linear alkyl group having 1 to 3 carbon atoms or a branched alkyl group having 3 carbon atoms. Specific examples thereof include a methyl group, an ethyl group, a n-propyl group, and an isopropyl group.

In the formula (4), t represents a number of 2 or 3, and from the viewpoint of acquisition of the raw materials for the production of organopolysiloxane, t is preferably 2.

The mass ratio (a/b) is in the range of from 80/20 to 95/5, preferably from 83/17 to 93/7, more preferably from 85/15 to 90/10 so that the resulting cosmetic composition is highly safe and achieves excellent adhesion and attachment to the skin.

Also, in the present specification, the mass ratio (a/b) refers to a value obtained from the integration ratio of the alkyl group or the phenyl group in the organopolysiloxane segment to the methylene group in the poly(N-acylalkyleneimine) segment as measured by nuclear magnetic resonance (¹H-NMR) analysis using deuterated chloroform in which 5% by mass of the organopolysiloxane of the component (E) is dissolved.

In the organopolysiloxane of the component (E), the weight average molecular weight (hereinbelow, sometimes also be simply referred to as "MWg") of the organopolysiloxane segment between adjacent poly(N-acylalkyleneimine) segments is in the range of from 10000 to 40000, and in consideration of the film flexibility and oil-water interfacial orientation, the above weight average molecular weight is more preferably from 15000 to 35000, even more preferably from 18000 to 32000.

According to the present invention, the "organopolysiloxane segment between adjacent poly(N-acylalkyleneimine) segments" indicates a segment surrounded by a broken line in the following formula (5), which is a segment between a linkage point of the poly(N-acylalkyleneimine) segment to the organopolysiloxane segment (shown as linkage point A) and a linkage point of the adjacent poly(N-acylalkyleneimine) segment (shown as linkage point B), comprising one $R^5SiO$ unit, one $R^6$, and the (y+1) number of $(R^5)_2SiO$ unit. Also, the "poly(N-acylalkyleneimine) segment" refers to the —Z—R⁷ moiety connected to the aforementioned $R^6$.

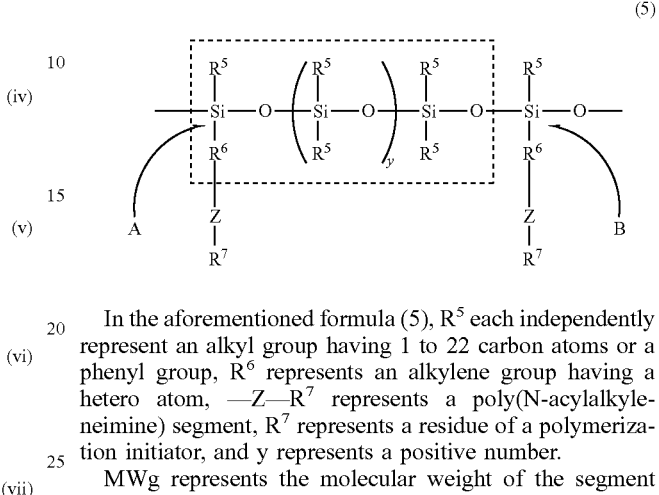

(5)

In the aforementioned formula (5), $R^5$ each independently represent an alkyl group having 1 to 22 carbon atoms or a phenyl group, $R^6$ represents an alkylene group having a hetero atom, —Z—R⁷ represents a poly(N-acylalkyleneimine) segment, $R^7$ represents a residue of a polymerization initiator, and y represents a positive number.

MWg represents the molecular weight of the segment surrounded by a broken line in the aforementioned formula (5), which can be interpreted as the mass of an organopolysiloxane segment per mole of poly(N-acylalkyleneimine) segment (g/mol). It is to be noted that when 100% of the functional groups of the modified organopolysiloxane, which serves as the raw material compound, are substituted with poly(N-acylalkyleneimine), MWg equals to the functional group equivalent (g/mol) of modified organopolysiloxane.

The molecular weight of the poly(N-acylalkyleneimine) segment can be calculated from the molecular weight and the degree of polymerization of N-acylalkyleneimine unit, or measured by gel permeation chromatography (hereinbelow, sometimes also be simply referred to as "GPC") method. It is to be noted that, according to the present invention, the molecular weight of the poly(N-acylalkyleneimine) segment refers to the number average molecular weight in terms of polystyrene (hereinbelow, sometimes also be simply referred to as "MNox") as measured by GPC measurement performed under the measurement conditions to be described later. When MNox is in the range of from 500 to 4000, the film flexibility and solubility in a solvent can be improved. From this viewpoint, the aforementioned MNox is preferably from 800 to 3500, more preferably from 1000 to 3000.

Also, the aforementioned MWg can be obtained based on the content ratio (% by mass) of the organopolysiloxane segment constituting the main chain (hereinbelow, sometimes also be simply referred to as "Csi") by the following formula (I).

$$MWg = Csi \times MNox/(100-Csi) \tag{I}$$

The weight average molecular weight of the organopolysiloxane segment constituting the main chain (hereinbelow, sometimes also be simply referred to as "MWsi") is from 50000 to 150000, and in consideration of flexibility and attachment to the skin, the weight average molecular weight of the organopolysiloxane segment constituting the main chain is preferably from 70000 to 130000, more preferably from 90000 to 110000. Also, the organopolysiloxane of the component (E) can be easily incorporated into various products by dissolving it in a polar solvent such as water. Because the organopolysiloxane segment constituting the main chain shares a common skeleton with the modified organopolysiloxane which serves as the raw material compound, MWsi is roughly equal to the weight average molecular weight of the modified organopolysiloxane which serves as the raw material compound. It should be noted that the weight average molecular weight of the modified organopolysiloxane, which serves as the raw material compound, is measured by GPC under the measurement conditions to be described later and expressed in terms of polystyrene.

From the viewpoint of achieving both of attachment to the skin and emulsion stability, the weight average molecular weight of the organopolysiloxane of the component (E) (hereinbelow, sometimes also be simply referred to as "MWt") is preferably from 60000 to 160000, more preferably from 80000 to 140000, and even more preferably from 100000 to 120000. The MWt value is measured by GPC under the measurement conditions to be described later and expressed in terms of polystyrene.

The organopolysiloxane of the component (E) has, in addition to a high elastic modulus and a large allowance for deformation, such unique thermoplasticity that when it is heated to a temperature range of 50 to 220° C., it becomes soft with markedly improved plasticity, but when the temperature drops to room temperature after heating is stopped, it immediately restores its elasticity.

The organopolysiloxane of the component (E) is produced by, for example, reacting a modified organopolysiloxane with a terminal reactive poly(N-acylalkyleneimine), the modified organopolysiloxane being represented by the following formula (6):

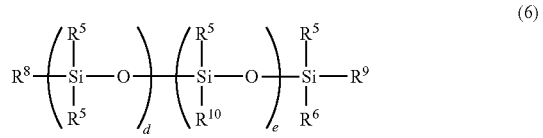

wherein, $R^5$ has the same meaning as above; and $R^8$ and $R^9$ each represent the same group as $R^5$ or a monovalent group represented by any of the following formulae (viii) to (xiii):

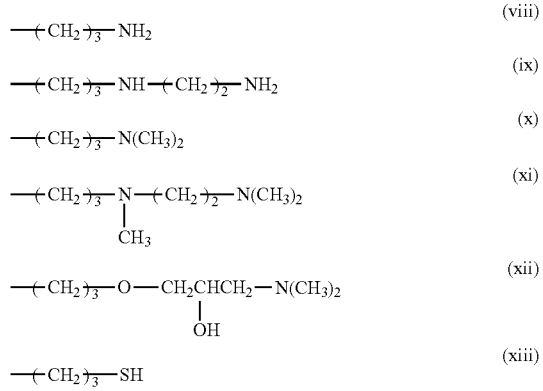

$R^{10}$ represents a monovalent group represented by the above formulae (viii) to (xiii); d represents a number of from 91.5 to 1255.0; and e represents a number of from 2.0 to 62.5; and the terminal reactive poly(N-acylalkyleneimine) being obtainable by ring-opening polymerization of a cyclic imino ether represented by the following formula (7):

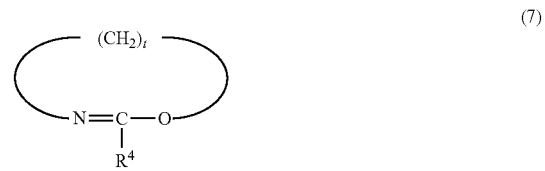

wherein, $R^4$ and t have the same meaning as above.

For the ring-opening polymerization of the cyclic imino ether represented by the formula (7) (hereinbelow, sometimes also be simply referred to as "cyclic imino ether (7)"), a polymerization initiator can be used. As the polymerization initiator, a compound having high electrophilic reactivity, for example, an alkyl ester of a strong acid such as alkylbenzene sulfonate, alkyl p-toluenesulfonate, alkyl trifluoromethanesulfonate, alkyl trifluoroacetate, and dialkyl sulfate, can be used. Among them, dialkyl sulfate is preferably used.

Examples of a solvent for polymerization include acetic acid esters such as ethyl acetate and propyl acetate, ethers such as diethyl ether, diisopropyl ether, dioxane, and tetrahydrofuran, ketones such as acetone and methyl ethyl ketone, a halogen solvent such as chloroform and methylene chloride, a nitrile solvent such as acetonitrile and benzonitrile, and an aprotic polar solvent such as N,N-dimethylformamide, N,N-dimethylacetamide, and dimethylsulfoxide. Among them, acetic acid esters are preferably used. The amount of the solvent used is normally from 20 to 2,000 parts by mass relative to 100 parts by mass of the cyclic imino ether (7).

The polymerization temperature is normally 30 to 170° C., preferably 40 to 150° C. Although the polymerization time varies depending on factors such as polymerization temperature, it is normally 1 to 60 hours.

For example, when 2-substituted-2-oxazoline is used as the cyclic imino ether (7), poly(N-acylethyleneimine) with t=2 in the above formula (4) can be obtained. When 2-substituted-dihydro-2-oxazine is used, poly(N-acylpropyleneimine) with t=3 in the above formula (4) can be obtained.

Poly(N-acylalkyleneimine) obtainable by the living polymerization of the cyclic imino ether (7) has a terminal reactive group. Therefore, the organopolysiloxane of the component (E) can be obtained by reacting the terminal reactive group of poly(N-acylalkyleneimine) with the reactive group represented by the above (viii) to (xiii) of the modified organopolysiloxane represented by the formula (6).

The production method by the living polymerization as described above is effective in that the degree of polymerization can be easily controlled by the amounts of the cyclic imino ether (7) and polymerization initiator used, as shown in the following theoretical formula (II), and also in that almost-monodisperse poly(N-acylalkyleneimine) having a narrower molecular weight distribution than that obtained with common radical polymerization can be obtained.

$$MNi = \frac{\text{Number of moles of cyclic imino ether (7)}}{\text{Number of moles of polymerization initiator}} \times$$

Molecular weight of cyclic imino ether (7) +

Molecular weight of polymerization initiator

[$MNi$; Calculated value of the number average molecular weight of poly($N$-acylalkyleneimine) obtainable by living polymerization]

The cyclic imino ether (7) and the polymerization initiator are used preferably in such amounts that MNi in the formula (II) is from 500 to 4000, more preferably in such amounts that MNi in the formula (II) is from 800 to 3500, and even more preferably in such amounts that MNi in the formula (II) is from 1000 to 3000.

From the viewpoint of solubility of the obtained organopolysiloxane in a polar solvent such as water and easiness in handling after dissolution, the weight average molecular weight of the modified organopolysiloxane represented by the formula (6) is preferably from 50000 to 150000, more preferably from 70000 to 130000, and even more preferably from 90000 to 110000.

Also, in order to satisfy the mass ratio (a/b) and MWg of the organopolysiloxane of the component (E), an upper limit is placed on the functional group equivalent of the modified organopolysiloxane represented by the formula (6). From this viewpoint as well as the viewpoint of providing the main chain with adequate hydrophobicity, the functional group equivalent is preferably from 10000 to 40000, more preferably from 15000 to 35000, and even more preferably from 18000 to 32000. At this point, the functional group equivalent of the modified organopolysiloxane represented by the formula (6) refers to a value obtained by dividing the weight average molecular weight of the modified organopolysiloxane represented by the formula (6) by the average number of $R^{10}$ per molecule of the modified organopolysiloxane.

From the viewpoint of the elastic modulus and allowance for deformation of the organopolysiloxane to be obtained, the modified organopolysiloxane represented by the formula (6) and the above terminal reactive poly(N-acylalkyleneimine) are used in such amounts that the mass ratio between them (modified organopolysiloxane/terminal reactive poly(N-acylalkyleneimine)) is in the range of preferably from 80/20 to 95/5, and from the same viewpoint, more preferably from 83/17 to 93/7, and even more preferably from 85/15 to 90/10.

According to the present invention, in the synthesis of each organopolysiloxane, the molecular weights of various molecules were measured in accordance with the following measurement conditions.

<Measurement Conditions for the Weight Average Molecular Weight of Modified Organopolysiloxane>

Column: Super HZ4000+Super HZ2000 (the product of Tosoh Corporation)
Eluent: 1 mM triethylamine/THF
Flow rate: 0.35 mL/min
Column temperature: 40° C.
Detector: UV
Sample: 50 µL <Measurement Conditions for MNox and MWt>

Column: K-804L (the product of Tosoh Corporation), two columns connected in series were used.
Eluent: 1 mM dimethyl dodecylamine/chloroform
Flow rate: 1.0 mL/min
Column temperature: 40° C.
Detector: RI
Sample: 50 µL Also, the $^1$H-NMR measurement for calculating the mass ratio (a/b) was performed under the following conditions.

<$^1$H-NMR Measurement Conditions>

The composition of the polymer thus obtained was confirmed by $^1$H-NMR (400 MHz, the product of Varian Medical Systems, Inc.).

A solution of 0.5 g of sample in 2 g of measurement solvent (deuterated chloroform) was measured.

Pulse Sequence

Relaxation delay: 30 seconds, Pulse: 45 degrees, Number of scans: 8

Peak confirmed Near 0 ppm: Methyl group in polydimethylsiloxane, Near 3.4 ppm: Methylene moiety in ethyleneimine The fractions of silicone and poly(N-propionylethyleneimine) were calculated from each integrated value.

Examples of the organopolysiloxane of the component (E) include poly(N-formylethyleneimine)organosiloxane, poly(N-acetylethyleneimine)organosiloxane, and poly(N-propionylethyleneimine)organosiloxane.

The component (E) can be used singly or in combination of two or more thereof, and the content thereof is, relative to the whole cosmetic composition, preferably 0.01% by mass or more, more preferably 0.1% by mass or more, and preferably 10% by mass or less, more preferably 5% by mass or less so that the resulting cosmetic composition is highly safe and achieves excellent adhesion and attachment to the skin. Also, the content of the component (E) is preferably from 0.01 to 10% by mass, more preferably from 0.1 to 5% by mass of the total composition.

In consideration of the durability of makeup and stability, in the present invention, the mass ratio of component (A) to component (E), (A)/(E), is preferably 0.1 or more, more preferably 1 or more, and preferably 100 or less, more preferably 60 or less. Also, the mass ratio of component (A) to component (E), (A)/(E), is preferably from 0.1 to 100, more preferably from 1 to 60.

In consideration of the feeling upon application and storage stability, the content of water used in the present invention is, relative to the whole cosmetic composition, preferably 10% by mass or more, more preferably 20% by mass or more, and preferably 60% by mass or less, more preferably 50% by mass or less. Also, the water content is preferably from 10 to 60% by mass, more preferably from 20 to 50% by mass of the total composition.

Examples of an oil agent used in the present invention include those remain liquid at 20° C., and when a solid or paste oil agent is used, it is preferable to dissolve it in another oil agent or solvent before use.

Examples of the oil agent used in the present invention include a silicone oil, a hydrocarbon oil, a higher fatty acid, a higher alcohol, an ester oil (including oil and fat), an ether oil, and a mineral oil. From the viewpoint of the feeling upon application, a silicone oil, a hydrocarbon oil, and an ester oil are preferable, of which a silicone oil is more preferable. Among silicone oils, dimethylpolysiloxane and cyclopolysiloxane are more preferable.

These oil agents can be used singly or in combination of two or more thereof.

Also, in consideration of the feeling upon application and storage stability, the content of the oil agent used in the present invention is, relative to the whole cosmetic composition, preferably 10% by mass or more, more preferably 20% by mass or more, and preferably 50% by mass or less, more preferably 40% by mass or less. Also, the content of the oil agent is preferably from 10 to 50% by mass, more preferably from 20 to 40% by mass of the total composition.

Also, examples of a surfactant used in the present invention include an anionic surfactant, a cationic surfactant, am amphoteric surfactant, and a nonionic surfactant. Among them, a nonionic surfactant is preferable, and a polyether-modified silicone is more preferable. From the viewpoint of stably emulsifying the components (A), (B), and (C), the HLB value is preferably 1 or more and 7 or less, more preferably 2 or more and 6 or less.

The content of the surfactant is, relative to the whole cosmetic composition, preferably 0.1% by mass or more, more preferably 0.2% by mass or more, and preferably 6% by mass or less, more preferably 3% by mass or less. Also, the content of the surfactant is preferably from 0.1 to 6% by mass, more preferably from 0.2 to 3% by mass of the total composition.

At this point, Hydrophilic-Lipophilic Balance (HLB) indicates the proportion of the molecular weight of the hydrophilic group moiety in the total molecular weight of the surfactant, and HLB of a nonionic surfactant can be obtained from the Griffin's formula.

HLB of a mixed surfactant composed of two or more nonionic surfactants can be obtained as follows. HLB of a mixed surfactant is a value obtained by calculating an arithmetic average of the HLB values of individual nonionic surfactants according to their blending ratios.

Mixed HLB=Σ(HLBx×Wx)/ΣWx

HLBx indicates the HLB value of a nonionic surfactant X.

Wx indicates the weight (g) of a nonionic surfactant X having a value of HLBx.

In addition to the above components, the cosmetic composition of the present invention can comprise components used in conventional cosmetic compositions, for example, a solid oil component such as Vaseline, lanolin, ceresin, microcrystalline wax, carnauba wax, and candelilla wax; a water-soluble or oil-soluble polymer; a powder other than the components mentioned above; ethanol, polyhydric alcohol, a preservative, an antioxidant, a dye, a thickener, a pH adjustor, a fragrance, an ultraviolet ray absorber, a humectant, a blood circulation-promoter, a cooling agent, an antiperspirant, a disinfectant, and a skin-revitalizing agent.

The cosmetic composition of the present invention can be produced in accordance with a common method, and it can be made into any emulsion type such as a water-in-oil type, an oil-in-water type, and a two-layer separation type. Among them, considering usability, a water-in-oil type emulsified cosmetic composition is preferable. Further, examples of the form include a liquid, an emulsion, a cream, and a gel, among which an emulsion is preferable.

The cosmetic composition of the present invention can be produced in accordance with a common method and provided as, for example, a makeup cosmetic composition such as a liquid foundation, an oil foundation, a powder foundation, a makeup base, a lipstick, a cheek blush, and an eyeshadow; and an ultraviolet protection cosmetic composition such as a sunscreen emulsion and a sunscreen cream. Among them, a liquid foundation, a makeup base, a sunscreen emulsion, and a sunscreen cream are preferable.

Pertaining to the aforementioned embodiments, the present invention further discloses the following compositions, production methods, or usage.

<1> A cosmetic composition, comprising the following components (A), (B), (C), and (D):

(A) from 0.01 to 48% by mass of a fluorine-modified silicone having a polysiloxane unit represented by the following formulae (1) and (2):

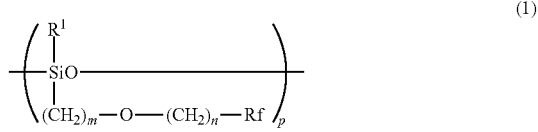

wherein, Rf represents a linear or branched perfluoroalkyl group having 6 carbon atoms; $R^1$, $R^2$, and $R^3$ are the same or different and each represent a linear or branched hydrocarbon group having 1 to 6 carbon atoms; m represents a number of from 2 to 6; n represents a number of from 1 to 6; p represents a number of from 3 to 50; s represents a number of from 1 to 5; and a ratio between p and s satisfies $0.66 \leq p/(p+s) \leq 0.9$, (B) from 0.01 to 40% by mass of a powder having been subjected to a surface treatment with tridecafluoro octyltriethoxysilane, (C) from 0.01 to 20% by mass of a fine zinc oxide particle having a specific surface area of 10 to 100 $m^2/g$, with the proviso that the component (B) is excluded from the component (C), and (D) octyl para-methoxycinnamate, wherein, a mass ratio of the component (A) to the component (D), (A)/(D), is from 0.5 to 10.

<2> The cosmetic composition according to the above <1>, wherein, a content of the component (A) is preferably from 0.1 to 30% by mass, more preferably from 1 to 20% by mass, and even more preferably from 4 to 15% by mass of the total composition.

<3> The cosmetic composition according to the above <1> or <2>, wherein, a content of the component (B) is preferably from 0.1 to 30% by mass, more preferably from 1 to 25% by mass, and even more preferably from 5 to 20% by mass of the total composition.

<4> The cosmetic composition according to any one of the above <1> to <3>, wherein, a mass ratio of the component (A) to the component (B), (A)/(B), is preferably from 0.01 to 50, more preferably from 0.1 to 20, even more preferably from 0.1 to 10, and further preferably from 0.2 to 2.

<5> The cosmetic composition according to any one of the above <1> to <4>, wherein, a content of the component (C) is preferably from 0.1 to 10% by mass, more preferably from 1 to 8% by mass of the total composition.

<6> The cosmetic composition according to any one of the above <1> to <5>, wherein, a mass ratio of the component (A) to the component (C), (A)/(C), is preferably from 0.1 to 10, more preferably from 0.9 to 7.

<7> The cosmetic composition according to any one of the above <1> to <6>, wherein, a content of the component (D) is preferably from 0.1 to 15% by mass, more preferably from 1 to 10% by mass of the total composition.

<8> The cosmetic composition according to any one of the above <1> to <7>, wherein, a mass ratio of the component (A) to the component (D), (A)/(D), is preferably from 1 to 5, more preferably from 1.3 to 4.

<9> The cosmetic composition according to any one of the above <1> to <8>, wherein, in the formulae (1) and (2) of the component (A), m is preferably from 2 to 5, more preferably 3; n is preferably from 1 to 4, more preferably 2; p is preferably from 3 to 10, more preferably from 3 to 6; and s is preferably from 1 to 3, more preferably 1.

<10> The cosmetic composition according to any one of the above <1> to <9>, wherein, in the formulae (1) and (2) of the component (A), a ratio of p/(p+s) satisfies preferably 0.66≤p/(p+s)≤0.9, more preferably 0.75≤p/(p+s)≤0.83.

<11> The cosmetic composition according to any one of the above <1> to <10>, wherein, an amount of tridecafluoro octyltriethoxysilane of the component (B) used in the treatment is preferably from 0.05 to 50% by mass, more preferably from 0.1 to 20% by mass.

<12> The cosmetic composition according to any one of the above <1> to <11>, wherein, the component (B) has an average particle diameter of preferably from 0.1 to 20 μm, more preferably from 0.1 to 10 μm.

<13> The cosmetic composition according to any one of the above <1> to <12>, wherein, the component (C) is preferably a fine zinc oxide particle having been subjected to a silicone treatment, more preferably a fine zinc oxide particle having been subjected to a silicone treatment with methyl hydrogen polysiloxane.

<14> The cosmetic composition according to any one of the above <1> to <13>, further comprising from 0.01 to 10% by mass of (E) an organopolysiloxane in which poly(N-acylalkyleneimine) segments are bound to at least two silicon atoms of an organopolysiloxane segment constituting a main chain via alkylene groups each having a hetero atom, the poly(N-acylalkyleneimine) segment comprising a repeating unit represented by the following formula (4):

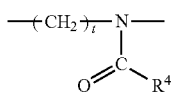

(4)

wherein, $R^4$ represents a hydrogen atom or an alkyl group having 1 to 3 carbon atoms and t represents 2 or 3, wherein, a number average molecular weight of the poly(N-acylalkyleneimine) segment is from 500 to 4000, a mass ratio of (a) the organopolysiloxane segment constituting the main chain to (b) the poly(N-acylalkyleneimine) segment, (a/b), is from 80/20 to 95/5, a weight average molecular weight of the organopolysiloxane segment between adjacent poly(N-acylalkyleneimine) segments is from 10000 to 40000, and a weight average molecular weight of the organopolysiloxane segment constituting the main chain is from 50000 to 150000.

<15> The cosmetic composition according to any one of the above <1> to <14>, wherein, a content of the component (E) is preferably from 0.01 to 10% by mass, more preferably from 0.1 to 5% by mass of the total composition.

<16> The cosmetic composition according to any one of the above <1> to <15>, wherein, a mass ratio of the components (A) to the component (E), (A)/(E), is preferably from 0.1 to 100, more preferably from 1 to 60.

<17> The cosmetic composition according to any one of the above <1> to <16>, wherein, the organopolysiloxane of the component (E) is produced by reacting a modified organopolysiloxane with a terminal reactive poly(N-acylalkyleneimine), the modified organopolysiloxane being represented by the following formula (6):

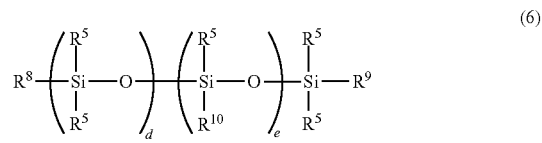

(6)

wherein, $R^5$ has the same meaning as above; and $R^8$ and $R^9$ each represent the same group as $R^5$ or a monovalent group represented by any of the following formulae (viii) to (xiii):

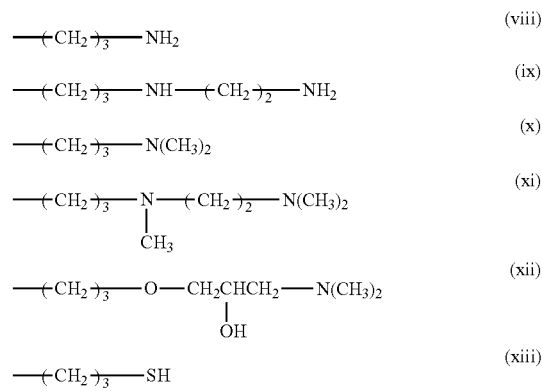

$R^{10}$ represents a monovalent group represented by the above formulae (viii) to (xiii); d represents a number of from 91.5 to 1255.0; and e represents a number of from 2.0 to 62.5; and the terminal reactive poly(N-acylalkyleneimine) being obtainable by ring-opening polymerization of a cyclic imino ether represented by the following formula (7):

(7)

wherein, $R^4$ and t have the same meaning as above, and wherein, a mass ratio of the modified organopolysiloxane represented by the formula (6) to the terminal reactive poly(N-acylalkyleneimine), (modified organopolysiloxane/terminal reactive poly(N-acylalkyleneimine)), is preferably from 80/20 to 95/5, more preferably from 83/17 to 93/7, and even more preferably from 85/15 to 90/10.

<18> The cosmetic composition according to any one of the above <1> to <17>, wherein, a water content is preferably from 10 to 60% by mass, more preferably from 20 to 50% by mass.

<19> The cosmetic composition according to any one of the above <1> to <18>, further comprising an oil agent which is liquid at 20° C., wherein, the oil agent is preferably at least one selected from the group consisting of a silicone oil, a hydrocarbon oil and an ester oil, more preferably a silicone oil, and even more preferably dimethylpolysiloxane or cyclopolysiloxane.

<20> The cosmetic composition according to the above <19>, wherein, a content of the oil agent which is liquid at 20° C. is preferably from 10 to 50% by mass, more preferably from 20 to 40% by mass.

<21> The cosmetic composition according to any one of the above <1> to <20>, further comprising a surfactant, wherein, the surfactant is preferably a nonionic surfactant, more preferably a polyether-modified silicone.

<22> The cosmetic composition according to the above <21>, wherein, the surfactant has an HLB value of preferably 1 or more and 7 or less, more preferably 2 or more and 6 or less.

<23> The cosmetic composition according to the above <21> or <22>, wherein, a content of the surfactant is preferably from 0.1 to 6% by mass, more preferably from 0.2 to 3% by mass.

<24> The cosmetic composition according to any one of the above <1> to <17>, which is preferably a water-in-oil type emulsified cosmetic composition, wherein, the cosmetic composition is preferably in a form of a liquid, an emulsion, a cream, or a gel, more preferably in a form of an emulsion.

<25> The cosmetic composition according to any one of the above <1> to <24>, which is preferably a liquid foundation, a makeup base, a sunscreen emulsion, or a sunscreen cream.

EXAMPLES

Synthetic Example 1 (Synthesis of Compound A1)

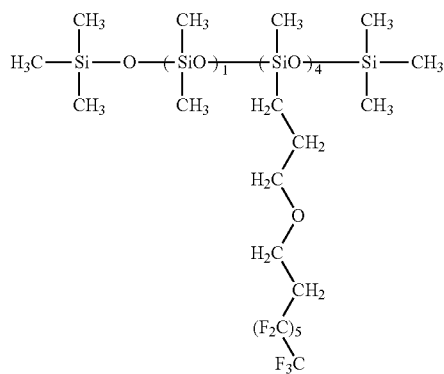

Synthesis of $C_6F_{13}$—$CH_2CH_2$—O—$CH_2CH$=$CH_2$

Into a 2 L four-necked flask equipped with a thermometer and a condenser pipe, 800 g (2.2 mol) of FA-6 (the product of Unimatec Co., Ltd.) and 175.78 g (4.4 mol) of granular NaOH (the product of Wako Pure Chemical Industries, Ltd.) were added. Under a nitrogen atmosphere, the flask was heated while stirring with a 12 cm crescent stirring blade made of Teflon (registered trade name) at 200 rpm to bring the temperature inside the flask to 60° C. To this flask, 398.73 g (3.3 mol) of allyl bromide (the product of Wako Pure Chemical Industries, Ltd.) was added dropwise over two hours. On completion of the dropwise addition, the resulting mixture was stirred at 70° C. for one hour, then at 80° C. for one hour. Subsequently, the temperature was raised to 130° C. to remove excess allyl bromide. After cooling to 60° C., 800 g of ion-exchanged water was added, followed by stirring for 30 minutes. The flask was then left to stand, and then phase separation was allowed to take place. After removing the resulting upper aqueous layer, 800 g of ion-exchanged water was further added, and the resulting mixture was once again stirred and left to stand, and the resulting aqueous layer was removed. The resulting product was dehydrated at 60° C./5 KPa and distilled at 100° C./2 KPa, whereby 774.9 g (yield 88%) of $C_6F_{13}$—$CH_2CH_2$—O—$CH_2CH$=$CH_2$ was obtained as a fraction of distillation.

Into a 300 mL four-necked flask equipped with a thermometer, 52.89 g (111 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.66 g of 2% by mass chloroplatinic acid hexahydrate/isopropyl alcohol was added and the temperature was raised to 110° C.

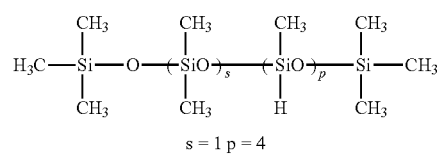

s = 1 p = 4

Then, 197.11 g (488 mmol) of $C_6F_{13}$—$CH_2CH_2$—O—$CH_2CH$=$CH_2$ was added dropwise over two hours. On completion of the dropwise addition, the resulting mixture was stirred at 110° C. for two hours, and then the temperature was dropped to 70° C. Subsequently, 25.07 g of a 0.1% NaOH solution was added, followed by stirring for two hours. The resulting mixture was dehydrated at 60° C./5 KPa, and on completion of dehydration, at the same temperature, 2.51 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 62.5 g of water at 100° C./5 KPa, whereby 206.3 g (yield 89%) of the compound of interest (Compound A1) was obtained.

Synthetic Example 2 (Synthesis of Compound A2)

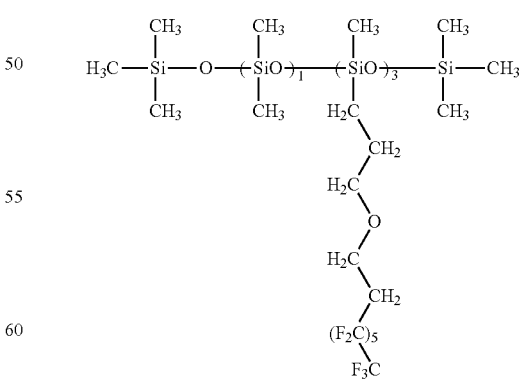

In a similar manner to Synthetic Example 1, $C_6F_{13}$—$CH_2CH_2$—O—$CH_2CH$=$CH_2$ was synthesized.

Into a 300 mL four-necked flask equipped with a thermometer, 21.29 g (51 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.26 g of 2% by mass chloroplatinic acid hexahydrate/isopropyl alcohol was added, and the temperature was raised to 110° C.

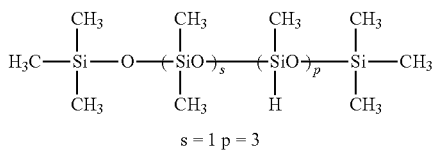

s = 1 p = 3

Then, 78.71 g (195 mmol) of $C_6F_{13}$—$CH_2CH_2$—O—$CH_2CH$=$CH_2$ was added dropwise over two hours. On completion of the dropwise addition, the resulting mixture was stirred at 110° C. for two hours, and then the temperature was dropped to 70° C. Subsequently, 10.03 g of a 0.1% NaOH solution was added, followed by stirring for two hours. The resulting mixture was dehydrated at 60° C./5 KPa, and on completion of dehydration, at the same temperature, 1.00 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 25 g of water at 100° C./5 KPa, whereby 78.9 g (yield 85%) of the compound of interest (Compound A2) was obtained.

Synthetic Example 3 (Synthesis of Compound A3)

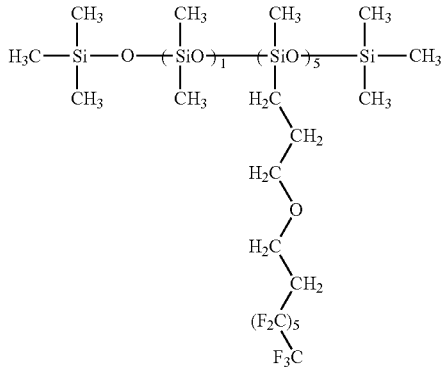

In a similar manner to Synthetic Example 1, $C_6F_{13}$—$CH_2CH_2$—O—$CH_2CH$=$CH_2$ was synthesized.

Into a 300 mL four-necked flask equipped with a thermometer, 17.61 g (33 mmol) of hydrogen polysiloxane (the product of Shin-Etsu Chemical Co., Ltd.) represented by the following formula was added, followed by stirring with an 8 cm crescent blade made of Teflon (registered trade name) at 200 rpm under a nitrogen atmosphere. Subsequently, 0.27 g of 2% by mass chloroplatinic acid hexahydrate/isopropyl alcohol was added, and the temperature was raised to 110° C.

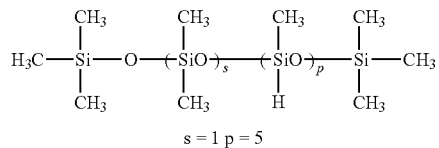

s = 1 p = 5

Then, 82.39 g (206 mmol) of $C_6F_{13}$—$CH_2CH_2$—O—$CH_2CH$=$CH_2$ was added dropwise over two hours. On completion of the dropwise addition, the resulting mixture was stirred at 110° C. for two hours, and then the temperature was dropped to 70° C. Subsequently, 10.03 g of a 0.1% NaOH solution was added, followed by stirring for two hours. The resulting mixture was dehydrated at 60° C./5 KPa, and on completion of dehydration, at the same temperature, 1.00 g of CARBORAFFIN 3 (the product of Japan EnviroChemicals, Ltd.) was added, followed by stirring for two hours. The resulting solution was filtered through a 0.1 μm PTFE membrane filter and the filtrate thus obtained was subjected to steam distillation with 25 g of water at 100° C./5 KPa, whereby 75.8 g (yield 82%) of the compound of interest (Compound A3) was obtained.

Synthetic Example 4 (Synthesis of Compound A4)

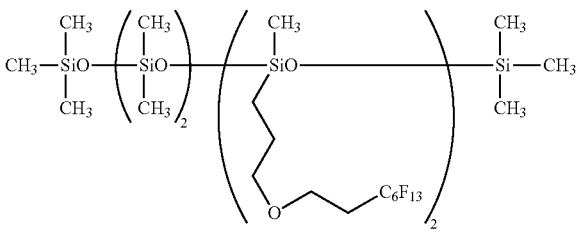

To a 100 mL two-necked flask equipped with a condenser pipe and a magnetic stirrer, under a nitrogen atmosphere, 20 mL of toluene, 8.0 g (18.6 mmol) of hydrogen polysiloxane ($MD_2D_2M^H$) (the product of Toshiba Silicones Co., Ltd.), 18.0 g (44.7 mmol) of $C_6F_{13}$—$CH_2CH_2$—O—$CH_2CH$=$CH_2$, and 29 μL ($0.89 \times 10^{-3}$ mmol) of a 2% solution of chloroplatinic acid in isopropyl alcohol were added, followed by stirring at 110° C. for four hours. The resulting reaction mixture was cooled to room temperature, to which 1.0 g of activated carbon was added, followed by stirring at room temperature for one hour. The activated carbon was filtered out and the solvent was distilled off. After distilling unreacted compounds off under reduced pressure, 20.3 g of the compound of interest (Compound A4) was obtained as a colorless, transparent oily substance (yield 87%).

Synthetic Example 5 (Synthesis of Compound A5)

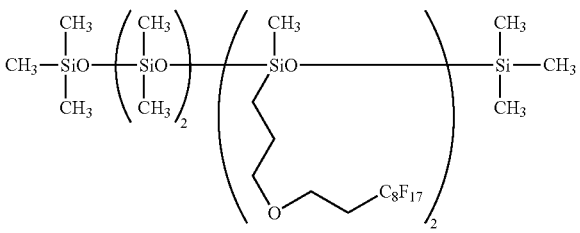

In a 100 mL two-necked flask equipped with a condenser pipe and a magnetic stirrer, under a nitrogen atmosphere, 19.0 g (44.1 mmol) of methyl hydrogen polysiloxane ($MD_2D^H{}_2M$) (the product of Toshiba Silicones Co., Ltd.) and 53.3 g (105.8 mmol) of $C_8F_{17}$—$CH_2CH_2$—O—$CH_2CH$=$CH_2$ were placed. Subsequently, after raising the temperature inside the flask to 80° C., 174.5 μL of a 2% solution of chloroplatinic acid in isopropyl alcohol was added, followed by stirring at 60° C. for five hours. After cooling the resulting reaction mixture to room temperature, 50 mL of hexane and 2.2 g of activated carbon were added, followed by stirring at room temperature for one hour. Subsequently, the activated carbon was filtered out and the solvent was distilled off. Unreacted compounds were then distilled off under reduced pressure, whereby 49.4 g of the compound of interest (Compound A5) was obtained as a colorless, transparent oily substance (yield 78%).

Synthetic Example 6

Synthesis of Compound OS-88

A mixture obtained by mixing 12.9 g (0.13 mol) of 2-ethyl-2-oxazoline and 27.7 g of ethyl acetate was dehydrated at 28° C. for 15 hours with 2.0 g of a molecular sieve (Zeolum A-4, the product of Tosoh Corporation).

Also, a mixed solution obtained by mixing 100 g of side chain primary aminopropyl-modified polydimethylsiloxane (KF-8015, the product of Shin-Etsu Chemical Co., Ltd., a weight average molecular weight of 100000, an amine equivalent of 20000) and 203 g of ethyl acetate was dehydrated at 28° C. for 15 hours with 15.2 g of a molecular sieve.

To the above dehydrated solution of 2-ethyl-2-oxazoline in ethyl acetate, 0.77 g (0.005 mol) of diethyl sulfate was added, followed by heating to reflux at 80° C. for eight hours under a nitrogen atmosphere, whereby terminal reactive poly(N-propionylethyleneimine) was synthesized. The number average molecular weight as measured by GPC was 2700.

The resulting terminal reactive poly(N-propionylethyleneimine) solution was added to the above dehydrated side chain primary aminopropyl-modified polydimethylsiloxane solution at once, followed by heating to reflux for 10 hours at 80° C.

The resulting reaction mixture was concentrated under reduced pressure, whereby a N-propionylethyleneimine-dimethylsiloxane copolymer was obtained as a white rubber-like solid (108 g). The mass fraction of the organopolysiloxane segment in the final product was 0.87, and the weight average molecular weight of the final product was 115000.

Examples 1 to 19 and Comparative Examples 1 to 5

W/O emulsion foundations having the compositions as shown in Tables 1 and 2 were produced, and the "stability" as well as "excellence in attachment to the skin", "moist feeling", and "durability of makeup" when each cosmetic composition was applied were evaluated. The results are collectively shown in Tables 1 and 2.

(Production Method)

With respect to Examples 1 to 19 and Comparative Examples 1 to 5, the components were weighed out based on a total weight of 100 g. For preliminary dispersion of oil phase, the oil phase (containing an activating agent) containing the component (A) was dispersed using a disperser (500 r/min, 5 minutes). Subsequently, a powder phase containing the components (B) and (C) was dispersed (1500 r/min, 10 minutes) in the oil phase. Homogeneous dispersion of the powder phase was confirmed. To the oil phase in which the powder phase was homogeneously dispersed, an ethanol phase was gradually added while stirring with a propeller (450 r/min). An aqueous phase component was then added over approximately 10 minutes and the resulting mixture was emulsified, and the emulsified state was maintained. Then, the viscosity was adjusted using a homomixer (3000 r/min) and defoaming was performed, whereby W/O emulsion foundations were obtained.

(Evaluation Method)

(1) Stability:

A 30 mL screw tube was filled with 20 mL of each W/O emulsion foundation. After storing the tubes under the conditions of 20° C. and 5° C., appearance of the W/O emulsion foundations after 24 hours, particularly the presence or absence of separation, was observed based on the following criteria.

A; The content is homogeneous.
B; A slight inconsistency is observed in the surface layer.
C; Separation of the oil layer is observed in the surface layer.
D; Separation is clearly observed.

(2) Excellence in attachment to the skin, moist feeling, and durability of makeup:

Fifteen expert panelists evaluated the "excellence in attachment to the skin" and "moist feeling" immediately after applying each W/O emulsion foundation to the skin using a sponge, and "durability of makeup" four hours after application based on the following criteria. The integrated values of 15 expert panelists are shown in Table 1.

(2-1) Excellence in attachment to the skin;
4; Excellent attachment to the skin.
3; Slightly excellent attachment to the skin.
2; Slightly poor attachment to the skin.
1; Poor attachment to the skin.

(2-2) Moist feeling;
4; Skin is moist after application.
3; Skin is slightly moist after application.
2; Skin is not very moist after application.
1; Skin is not moist after application.

(2-3) Durability of makeup;
4; Excellent durability of makeup is observed.
3; Slightly excellent durability of makeup is observed.
2; Slightly poor durability of makeup is observed.
1; Poor durability of makeup is observed.

TABLE 1

| Component (% by mass) | | | 1 | 2 | 3 | 4 | 5 | 6 | 7 | 8 | 9 | 10 | 11 | 12 |
|---|---|---|---|---|---|---|---|---|---|---|---|---|---|---|
| Oil phase | (A) | Fluorine-modified silicone (Synthetic Example 1) | 7.0 | — | — | — | — | 7.0 | 7.0 | 7.0 | 7.0 | 7.0 | 7.0 | 1.7 |
| | | Fluorine-modified silicone (Synthetic Example 2) | — | 7.0 | — | — | — | — | — | — | — | — | — | — |
| | | Fluorine-modified silicone (Synthetic Example 3) | — | — | 7.0 | — | — | — | — | — | — | — | — | — |
| | | Fluorine-modified silicone (Synthetic Example 4) | — | — | — | 4.0 | — | — | — | — | — | — | — | — |
| | | Fluorine-modified silicone (Synthetic Example 5) | — | — | — | — | 15.0 | — | — | — | — | — | — | — |
| Powder phase | (B) | Titanium oxide treated with 5% by mass tridecafluoro octyltriethoxysilane | 7.5 | 7.5 | 7.5 | 7.5 | 7.5 | 7.5 | 7.5 | 2.17 | 8.8 | 7.5 | 7.5 | 7.5 |
| | | Red iron oxide treated with 5% by mass tridecafluoro octyltriethoxysilane | 0.4 | 0.4 | 0.4 | 0.4 | 0.4 | 0.4 | 0.4 | 0.1 | 0.5 | 0.4 | 0.4 | 0.4 |
| | | Yellow iron oxide treated with 5% by mass tridecafluoro octyltriethoxysilane | 2.0 | 2.0 | 2.0 | 2.0 | 2.0 | 2.0 | 2.0 | 0.6 | 2.3 | 2.0 | 2.0 | 2.0 |
| | | Black iron oxide treated with 5% by mass tridecafluoro octyltriethoxysilane | 0.1 | 0.1 | 0.1 | 0.1 | 0.1 | 0.1 | 0.1 | 0.03 | 0.2 | 0.1 | 0.1 | 0.1 |
| | | Titanium mica treated with 3% by mass tridecafluoro octyltriethoxysilane | 4.0 | 4.0 | 4.0 | 4.0 | 4.0 | 4.0 | 4.0 | 1.2 | 4.7 | 4.0 | 4.0 | 4.0 |
| | | Nylon powder treated with 5% by mass tridecafluoro octyltriethoxysilane | 2.0 | 2.0 | 2.0 | 2.0 | 2.0 | 2.0 | 2.0 | 0.6 | 2.3 | 2.0 | 2.0 | 2.0 |
| | | Silica treated with 3% by mass tridecafluoro octyltriethoxysilane | 1.0 | 1.0 | 1.0 | 1.0 | 1.0 | 1.0 | 1.0 | 0.3 | 1.2 | 1.0 | 1.0 | 1.0 |
| | Other components | Titanium oxide treated with 5% by mass perfluoroalkyl phosphate ester | — | — | — | — | — | — | — | — | — | — | — | — |
| | | Red iron oxide treated with 5% by mass perfluoroalkyl phosphate ester | — | — | — | — | — | — | — | — | — | — | — | — |
| | | Yellow iron oxide treated with 5% by mass perfluoroalkyl phosphate ester | — | — | — | — | — | — | — | — | — | — | — | — |
| | | Black iron oxide treated with 5% by mass perfluoroalkyl phosphate ester | — | — | — | — | — | — | — | — | — | — | — | — |
| | | Titanium mica treated with 3% by mass perfluoroalkyl phosphate ester | — | — | — | — | — | — | — | — | — | — | — | — |
| | | Nylon powder treated with 5% by mass perfluoroalkyl phosphate ester | — | — | — | — | — | — | — | — | — | — | — | — |
| | | Silica treated with 3% by mass perfluoroalkyl phosphate ester | — | — | — | — | — | — | — | — | — | — | — | — |
| | (C) | Fine zinc oxide particles treated with 6% by mass silicone (FINEX-50, specific surface area 45 m$^2$/g) | 3.0 | 3.0 | 3.0 | 3.0 | 3.0 | 1.0 | 8.0 | 3.0 | 3.0 | 3.0 | 3.0 | 3.0 |
| Oil phase | (D) | Octyl para-methoxycinnamate (Uvinul MC80) | 3.0 | 3.0 | 3.0 | 3.0 | 3.0 | 3.0 | 3.0 | 3.0 | 3.0 | 3.0 | 3.0 | 3.0 |
| Ethanol phase | (E) | Oxazoline-modified silicone (Synthetic Example 6) | — | — | — | — | — | — | — | — | — | 1.0 | 3.0 | — |
| | Other components | Ethanol | — | — | — | — | — | — | — | — | — | 5.0 | 5.0 | — |
| Oil phase | Other components | Dimethylpolysiloxane-polyoxyalkylene copolymer (Dow Corning Toray Co., Ltd. Silicone SH3775M) | 0.5 | 0.5 | 0.5 | 0.5 | 0.5 | 0.5 | 0.5 | 0.5 | 0.5 | 0.5 | 0.5 | 0.5 |
| | | Decamethylcyclopentasiloxane (the product of Dow Corning Toray Co., Ltd.) | 15.0 | 15.0 | 15.0 | 15.0 | 15.0 | 15.0 | 15.0 | 15.0 | 15.0 | 15.0 | 15.0 | 15.0 |
| | | Dimethylpolysiloxane (Dow Corning Toray Co., Ltd., Silicone SH200 C Fluid 2CS) | 15.0 | 15.0 | 15.0 | 15.0 | 15.0 | 15.0 | 15.0 | 15.0 | 15.0 | 15.0 | 15.0 | 15.0 |
| Aqueous phase | | Magnesium sulfate | 0.7 | 0.7 | 0.7 | 0.7 | 0.7 | 0.7 | 0.7 | 0.7 | 0.7 | 0.7 | 0.7 | 0.7 |
| | | Glycerol | 1.0 | 1.0 | 1.0 | 1.0 | 1.0 | 1.0 | 1.0 | 1.0 | 1.0 | 1.0 | 1.0 | 1.0 |
| | | Purified water | Balance | Balance | Balance | Balance | Balance | Balance | Balance | Balance | Balance | Balance | Balance | Balance |
| | | Total | 100 | 100 | 100 | 100 | 100 | 100 | 100 | 100 | 100 | 100 | 100 | 100 |
| | | Sum of (B) | 17 | 17 | 17 | 17 | 17 | 17 | 17 | 5 | 20 | 17 | 17 | 17 |
| | | (A)/(B) | 0.41 | 0.41 | 0.41 | 0.24 | 0.88 | 0.41 | 0.41 | 1.40 | 0.35 | 0.41 | 0.41 | 0.10 |
| | | (A)/(C) | 2.3 | 2.3 | 2.3 | 1.3 | 5.0 | 7.0 | 0.9 | 2.3 | 2.3 | 2.3 | 2.3 | 0.6 |
| | | (A)/(D) | 2.3 | 2.3 | 2.3 | 1.3 | 5.0 | 2.3 | 2.3 | 2.3 | 2.3 | 2.3 | 2.3 | 0.6 |
| Effect | | Stability 5° C. (1-day storage) | A | A | A | A | A | A | A | A | A | A | A | A |
| | | Stability 20° C. (1-day storage) | A | A | A | A | B | A | A | B | B | A | A | A |
| | | Excellence in attachment to the skin | 48 | 42 | 45 | 42 | 41 | 42 | 41 | 42 | 41 | 49 | 54 | 40 |
| | | Moist feeling | 47 | 43 | 53 | 43 | 40 | 48 | 40 | 40 | 41 | 52 | 53 | 41 |
| | | Durability of makeup | 47 | 44 | 50 | 51 | 41 | 40 | 49 | 40 | 43 | 52 | 55 | 48 |

TABLE 2

| | Component (% by mass) | Example 13 | Example 14 | Example 15 | Example 16 | Example 17 | Example 18 | Example 19 | Comp. 1 | Comp. 2 | Comp. 3 | Comp. 4 | Comp. 5 |
|---|---|---|---|---|---|---|---|---|---|---|---|---|---|
| Oil phase (A) | Fluorine-modified silicone (Synthetic Example 1) | 30.0 | 7.0 | 7.0 | 7.0 | 7.0 | 7.0 | 7.0 | 7.0 | — | — | — | — |
| | Fluorine-modified silicone (Synthetic Example 2) | — | 0.375 | — | — | — | — | — | — | — | — | — | — |
| | Fluorine-modified silicone (Synthetic Example 3) | — | 0.020 | — | — | — | — | — | — | — | — | — | — |
| | Fluorine-modified silicone (Synthetic Example 4) | — | 0.100 | — | — | — | — | — | — | — | — | — | — |
| Other components | Fluorine-modified silicone (Synthetic Example 5) | — | 0.005 | — | — | — | — | — | — | 7.0 | 7.0 | 7.0 | 7.0 |
| Powder phase (B) | Titanium oxide treated with 5% by mass tridecafluoro octyltriethoxysilane | 7.5 | 0.100 | 7.5 | 7.5 | 7.5 | 7.5 | 7.5 | 7.5 | 7.5 | — | 7.5 | 7.5 |
| | Red iron oxide treated with 5% by mass tridecafluoro octyltriethoxysilane | 0.4 | 0.050 | 0.4 | 0.4 | 0.4 | 0.4 | 0.4 | 0.4 | 0.4 | — | 0.4 | 0.4 |
| | Yellow iron oxide treated with 5% by mass tridecafluoro octyltriethoxysilane | 2.0 | — | 2.0 | 2.0 | 2.0 | 2.0 | 2.0 | 2.0 | 2.0 | — | 2.0 | 2.0 |
| | Black iron oxide treated with 5% by mass tridecafluoro octyltriethoxysilane | 0.1 | — | 0.1 | 0.1 | 0.1 | 0.1 | 0.1 | 0.1 | 0.1 | — | 0.1 | 0.1 |
| | Titanium mica treated with 3% by mass tridecafluoro octyltriethoxysilane | 4.0 | — | 4.0 | 4.0 | 4.0 | 4.0 | 4.0 | 4.0 | 4.0 | — | 4.0 | 4.0 |
| | Nylon powder treated with 5% by mass tridecafluoro octyltriethoxysilane | 2.0 | — | 2.0 | 2.0 | 2.0 | 2.0 | 2.0 | 2.0 | 2.0 | — | 2.0 | 2.0 |
| | Silica treated with 3% by mass tridecafluoro octyltriethoxysilane | 1.0 | — | 1.0 | 1.0 | 1.0 | 1.0 | 1.0 | 1.0 | 1.0 | — | 1.0 | 1.0 |
| Other components | Titanium oxide treated with 5% by mass perfluoroalkyl phosphate ester | — | — | — | — | — | — | — | — | — | 7.5 | — | 7.5 |
| | Red iron oxide treated with 5% by mass perfluoroalkyl phosphate ester | — | — | — | — | — | — | — | — | — | 0.4 | — | 0.4 |
| | Yellow iron oxide treated with 5% by mass perfluoroalkyl phosphate ester | — | — | — | — | — | — | — | — | — | 2.0 | — | 2.0 |
| | Black iron oxide treated with 5% by mass perfluoroalkyl phosphate ester | — | — | — | — | — | — | — | — | — | 0.1 | — | 0.1 |
| | Titanium mica treated with 3% by mass perfluoroalkyl phosphate ester | — | — | — | — | — | — | — | — | — | 4.0 | — | 4.0 |
| | Nylon powder treated with 5% by mass perfluoroalkyl phosphate ester | — | — | — | — | — | — | — | — | — | 2.0 | — | 2.0 |
| | Silica treated with 3% by mass perfluoroalkyl phosphate ester | — | — | — | — | — | — | — | — | — | 1.0 | — | 1.0 |
| (C) | Fine zinc oxide particles treated with 6% by mass silicone (FINEX-50, specific surface area 45 m²/g) | 3.0 | 3.0 | 20.0 | 3.0 | 3.0 | 3.0 | 3.0 | 3.0 | 3.0 | 3.0 | 3.0 | 3.0 |
| Oil phase (D) | Octyl para-methoxycinnamate (Uvinul MC80) | 3.0 | 3.0 | 3.0 | 0.2 | 1.0 | 10.0 | 3.0 | 3.0 | 3.0 | 3.0 | 3.0 | 3.0 |
| Ethanol phase (E) | Oxazoline-modified silicone (Synthetic Example 6) | — | — | — | — | — | — | 0.2 | — | — | — | — | — |
| Other components | Ethanol | — | — | — | — | — | — | 5.0 | — | — | — | — | — |
| Oil phase | Dimethylpolysiloxane-polyoxyalkylene copolymer (Dow Corning Toray Co., Ltd., Silicone SH3775M) | 0.5 | 0.5 | 0.5 | 0.5 | 0.5 | 0.5 | 0.5 | 0.5 | 0.5 | 0.5 | 0.5 | 0.5 |
| Other components | Decamethylcyclopentasiloxane (the product of Dow Corning Toray Co., Ltd., SH245) | 15.0 | 15.0 | 15.0 | 15.0 | 15.0 | 15.0 | 15.0 | 15.0 | 15.0 | 15.0 | 15.0 | 15.0 |
| | Dimethylpolysiloxane (the product of Dow Corning Toray Co., Ltd., Silicone SH200 C Fluid 2CS) | 15.0 | 15.0 | 15.0 | 15.0 | 15.0 | 15.0 | 15.0 | 15.0 | 15.0 | 15.0 | 15.0 | 15.0 |
| Aqueous phase | Magnesium sulfate | 0.7 | 0.7 | 0.7 | 0.7 | 0.7 | 0.7 | 0.7 | 0.7 | 0.7 | 0.7 | 0.7 | 0.7 |
| | Glycerol | 1.0 | 1.0 | 1.0 | 1.0 | 1.0 | 1.0 | 1.0 | 1.0 | 1.0 | 1.0 | 1.0 | 1.0 |
| | Purified water | Balance | Balance | Balance | Balance | Balance | Balance | Balance | Balance | Balance | Balance | Balance | Balance |
| | Total | 100 | 100 | 100 | 100 | 100 | 100 | 100 | 100 | 100 | 100 | 100 | 100 |
| | Sum of (B) | 17 | 1 | 17 | 17 | 17 | 17 | 17 | 17 | 17 | 17 | 17 | 17 |
| | (A)/(B) | 1.76 | 8.24 | 0.41 | 0.41 | 0.41 | 0.41 | 0.41 | — | — | — | — | — |
| | (A)/(C) | 10.0 | 2.3 | 0.4 | 2.3 | 2.3 | 2.3 | 2.3 | 2.3 | — | — | — | — |
| | (A)/(D) | 10.0 | 2.3 | 2.3 | 35.0 | 7.0 | 0.7 | 2.3 | 2.3 | — | — | — | — |
| Effect | Stability 5° C. (1-day storage) | B | A | A | A | A | A | A | B | B | B | B | C |
| | Stability 20° C. (1-day storage) | B | A | A | A | A | B | A | D | C | D | C | C |
| | Excellence in attachment to the skin | 40 | 43 | 36 | 41 | 40 | 38 | 50 | 35 | 41 | 37 | 33 | 37 |
| | Moist feeling | 38 | 42 | 37 | 42 | 44 | 39 | 51 | 37 | 35 | 33 | 34 | 33 |
| | Durability of makeup | 39 | 37 | 55 | 50 | 49 | 40 | 50 | 51 | 38 | 42 | 45 | 53 |

Example 20 (Liquid Foundation)

(Composition)

| | |
|---|---|
| (1) Dimethylpolysiloxane-polyoxyalkylene copolymer (product of Shin-Etsu Chemical Co., Ltd., Silicone KF-6015) | 0.5 (% by mass) |
| (2) Fluorine-modified silicone (Synthetic Example 1) | 7.0 |
| (3) Decamethylcyclopentasiloxane (product of Dow Corning Toray Co., Ltd., Silicone SH245) | 12.0 |
| (4) Dimethylpolysiloxane (product of Shin-Etsu Chemical Co., Ltd., Silicone KF-96A1CS) | 5.0 |
| (5) Dimethylpolysiloxane (product of Shin-Etsu Chemical Co., Ltd., Silicone KF-96L2CS) | 15.0 |
| (6) Octyl para-methoxycinnamate | 3.0 |
| (7) Fragrance | trace |
| (8) 1,3-Butylene glycol | 1.0 |
| (9) 86% Glycerol | 0.5 |
| (10) Ethanol | 3.0 |
| (11) Purified water | balance |
| (12) Titanium oxide treated with 5% by mass FHS | 7.0 |
| (13) Red iron oxide treated with 5% by mass FHS | 0.5 |
| (14) Yellow iron oxide treated with 5% by mass FHS | 2.0 |
| (15) Black iron oxide treated with 5% by mass FHS | 0.2 |
| (16) Titanium mica treated with 3% by mass FHS | 2.0 |
| (17) Tospearl treated with 5% by mass FHS | 1.8 |
| (18) Mica treated with 3% by mass FHS | 2.5 |
| (19) Fine zinc oxide particle treated with silicone (Silicone-treated FINEX-S, specific surface area 75 m$^2$/g) | 3.0 |
| Total | 100 |

(Production Method)

After roughly mixing the powder components (12) to (19), the resulting powder mixture was mixed and ground by an atomizer grinding machine (the product of Fuji Paudal Co., Ltd.). The oil phase components (1) to (7) were mixed by stirring, to which the ground powder components were added, followed by dispersion using a disperser. The aqueous phase components (8) to (11) were mixed and then added to the oil phase components, followed by emulsification. The viscosity was then adjusted by a homomixer, whereby a liquid foundation was obtained.

Example 21 (Makeup Base)

(Composition)

| | |
|---|---|
| (1) Dimethylpolysiloxane-polyoxyalkylene copolymer (Dow Corning Toray Co., Ltd., Silicone SH3775M) | 0.6 (% by mass) |
| (2) Fluorine-modified silicone (Synthetic Example 1) | 10.0 |
| (3) Decamethylcyclopentapolysiloxane (product of Dow Corning Toray Co., Ltd., Silicone SH245) | 25.0 |
| (4) Dimethylpolysiloxane (product of Shin-Etsu Chemical Co., Ltd., Silicone KF-96L2CS) | 15.0 |
| (5) Octyl para-methoxycinnamate | 1.0 |
| (6) Preservative | q.s. |
| (7) Propylene glycol | 1.5 |
| (8) Purified water | balance |
| (9) Ethanol | 4.0 |
| (10) Treated with 5% by mass FHS | 0.01 |
| (11) Nylon powder treated with 5% by mass FHS | 1.99 |
| (12) Talc treated with 5% by mass FHS | 3.0 |
| (13) Sericite treated with 5% by mass FHS | 1.0 |
| (14) Fine zinc oxide particles treated with silicone (MICRO ZINC OXIDE MZ-504R3M, specific surface area 40 m$^2$/g) | 3.0 |
| Total | 100 |

(Production Method)

After roughly mixing the powder components (10) to (14), the resulting powder mixture was mixed and ground by an atomizer grinding machine (the product of Fuji Paudal Co., Ltd.). The oil phase components (1) to (6) were mixed by stirring, to which the ground powder components were added, followed by dispersion using a disperser. The aqueous phase components (7) to (9) were mixed and then added to the oil phase components, followed by emulsification. The viscosity was then adjusted by a homomixer, whereby a makeup base was obtained.

Example 22 (UV Cosmetic Composition)

(Composition)

| | |
|---|---|
| (1) Dimethylpolysiloxane-polyoxyalkylene copolymer (product of Dow Corning Toray Co., Ltd., Silicone SH3775M) | 0.5 (% by mass) |
| (2) Fluorine-modified silicone (Synthetic Example 2) | 10.0 |
| (3) Decamethylcyclopentapolysiloxane (product of Dow Corning Toray Co., Ltd., Silicone SH245) | 25.0 |
| (4) Dimethylpolysiloxane (product of Shin-Etsu Chemical Co., Ltd., Silicone KF-96L2CS) | 15.0 |
| (5) Octyl para-methoxycinnamate | 4.0 |
| (6) Preservative | q.s. |
| (7) Propylene glycol | 1.5 |
| (8) Purified water | balance |
| (9) Ethanol | 5.0 |
| (10) Fine titanium oxide particles treated with 7% by mass FHS | 7.0 |
| (11) Nylon powder treated with 3% by mass FHS | 2.0 |
| (12) Talc treated with 5% by mass FHS | 2.0 |
| (13) Fine zinc oxide particles treated with silicone (MICRO ZINC OXIDE MZ-504R3M, specific surface area 40 m$^2$/g) | 7.0 |
| Total | 100 |

(Production Method)

After roughly mixing the powder components (10) to (13), the resulting powder mixture was mixed and ground by an atomizer grinding machine (the product of Fuji Paudal Co., Ltd.). The oil phase components (1) to (6) were mixed by stirring, to which the ground powder components were added, followed by dispersion using a disperser. The aqueous phase components (7) to (9) were mixed and then added to the oil phase components, followed by emulsification. The viscosity was then adjusted by a homomixer, whereby a UV cosmetic composition was obtained.

All of the cosmetic compositions obtained in Examples 20 to 22 are highly safe, and when they are applied, they exhibit excellent adhesion and attachment to the skin and provide a moist feeling, and makeup lasts for a long time.

The invention claimed is:

1. A cosmetic composition, comprising components (A), (B), (C), and (D):
    (A) from 1 to 20% by mass of a fluorine-modified silicone having a polysiloxane unit represented by formulae (1) and (2):

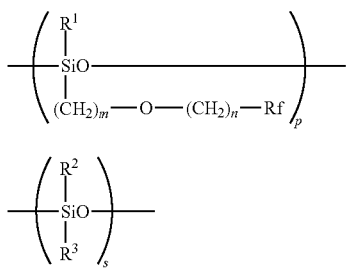

wherein,
Rf represents a linear or branched perfluoroalkyl group having 6 carbon atoms;
$R^1$, $R^2$, and $R^3$ are the same or different and each represent a linear or branched hydrocarbon group having 1 to 6 carbon atoms;
m represents a number of from 2 to 6;
n represents a number of from 1 to 6;
p represents a number of from 3 to 50;
s represents a number of from 1 to 5; and
a ratio between p and s satisfies $0.66 < p/(p+s) < 0.9$, (B) from 0.01 to 40% by mass of a powder having been subjected to a surface treatment with tridecafluoro octyltriethoxysilane, (C) from 0.01 to 20% by mass of fine zinc oxide particles having a specific surface area of from 10 to 100 m²/g, with the proviso that the component (B) is excluded from the component (C), and (D) octyl para-methoxycinnamate,
wherein, a mass ratio of the component (A) to the component (D), (A)/(D), is from 0.5 to 10.

2. The cosmetic composition according to claim 1, wherein a content of the component (D) is from 0.1 to 15% by mass.

3. The cosmetic composition according to claim 1, wherein a content of the component (B) is from 1 to 20% by mass, a content of the component (C) is from 1 to 20% by mass, and a content of the component (D) is from 1 to 10% by mass.

4. The cosmetic composition according to claim 1, wherein a mass ratio of the component (A) to the component (C), (A) / (C), is from 0.1 to 10.

5. The cosmetic composition according to claim 1, wherein a mass ratio of the component (A) to the component (B), (A) / (B), is from 0.1 to 10.

6. The cosmetic composition according to claim 1, further comprising from 0.01 to 10% by mass of (E) an organopolysiloxane in which poly(N-acylalkyleneimine) segments are bound to at least two silicon atoms of an organopolysiloxane segment constituting a main chain via alkylene groups each having a hetero atom, the poly(N-acylalkyleneimine) segment comprising a repeating unit represented by formula (4):

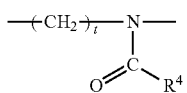

wherein, $R^4$ represents a hydrogen atom or an alkyl group having 1 to 3 carbon atoms and t represents 2 or 3, wherein, a number average molecular weight of the poly(N-acylalkyleneimine) segment is from 500 to 4000,
a mass ratio of (a) the organopolysiloxane segment constituting the main chain to (b) the poly(N-acylalkyleneimine) segment, (a / b), is from 80/20 to 95/5,
a weight average molecular weight of the organopolysiloxane segment between adjacent poly(N-acylalkyleneimine) segments is from 10000 to 40000, and
a weight average molecular weight of the organopolysiloxane segment constituting the main chain is 50000 to 150000.

7. The cosmetic composition according to claim 6, wherein, a mass ratio of the component (A) to the component (E), (A) / (E), is from 0.1 to 100.

8. The cosmetic composition according to claim 6, wherein, the organopolysiloxane of the component (E) is produced by reacting a modified organopolysiloxane with a terminal reactive poly(N-acylalkyleneimine), the modified organopolysiloxane being represented by formula (6):

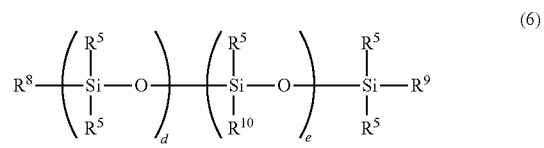

wherein, $R^5$ each independently represent an alkyl group having 1 to 22 carbon atoms or a phenyl group; and $R^8$ and $R^9$ each represent the same group as $R^5$ or a monovalent group represented by any of the following formulae (viii) to (xiii):

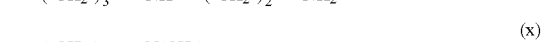

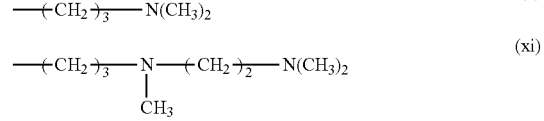

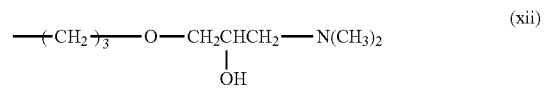

$R^{10}$ represents a monovalent group represented by the above formulae (viii) to (xiii); d represents a number of from 91.5 to 1255.0; and e represents a number of from 2.0 to 62.5, and
the terminal reactive poly(N-acylalkyleneimine) being obtainable by ring-opening polymerization of a cyclic imino ether represented by the following formula (7):

wherein, $R^4$ and t have the same meaning as above, and wherein, a mass ratio of the modified organopolysiloxane represented by the formula (6) to the terminal reactive poly(N-acylalkyleneimine), (modified organopolysiloxane / terminal reactive poly(N-acylalkyleneimine)), is from 83/17 to 93/7.

9. The cosmetic composition according to claim 8, wherein a mass ratio of the modified organopolysiloxane represented by the formula (6) to the terminal reactive poly(N-acylalkyleneimine), modified organopolysiloxane / terminal reactive poly(N-acylalkyleneimine), is from 85/15 to 90/10.

10. The cosmetic composition according to claim 1, wherein, in the formulae (1) and (2) of the component (A), m is from 2 to 5; n is from 1 to 4; p is from 3 to 10; and s is from 1 to 3.

11. The cosmetic composition according to claim 1, wherein, in the formulae (1) and (2) of the component (A), a ratio of p/(p+s) satisfies $0.75 \leq p/(p+s) \leq 0.83$.

12. The cosmetic composition according to claim 1, wherein the component (B) has an average particle diameter of from 0.1 to 20 μm.

13. The cosmetic composition according to claim 1, wherein, the component (C) is a fine zinc oxide particle having been subjected to a silicone treatment.

14. The cosmetic composition according to claim 1, wherein, a water content is from 10 to 60% by mass.

15. The cosmetic composition according to claim 1, further comprising an oil agent which is liquid at 20° C., which is at least one selected from the group consisting of a silicone oil, a hydrocarbon oil and an ester oil, wherein a content thereof is from 10 to 50% by mass.

16. The cosmetic composition according to claim 1, further comprising a surfactant, wherein the surfactant is a nonionic surfactant.

17. The cosmetic composition according to claim 16, wherein the surfactant is a polyether-modified silicone.

18. The cosmetic composition according to claim 16, wherein the nonionic surfactant has an HLB value of 1 or more and 7 or less.

19. The cosmetic composition according to claim 16, wherein a content of the surfactant is from 0.1 to 6% by mass.

20. The cosmetic composition according to claim 1, wherein the cosmetic composition is a water-in-oil type emulsified cosmetic composition.

21. The cosmetic composition according to claim 1, which is a liquid foundation, a makeup base, a sunscreen emulsion, or a sunscreen cream.

22. A method for using the cosmetic composition according to claim 1, comprising applying the composition to the skin using a sponge.

23. The cosmetic composition according to claim 1, wherein the composition remains homogenous after storing at 5° C. for 24 hours.

24. A cosmetic composition, comprising components (A), (B), (C), and (D):
(A) from 1 to 20% by mass of a fluorine-modified silicone of formula (3):

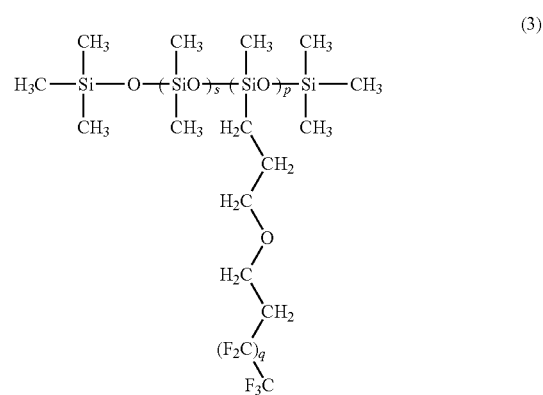

wherein,
p represents a number of from 3 to 10;
s represents a number of from 1 to 3;
q is 5; and
a ratio between p and s satisfies $0.66 < p/(p+s) \leq 0.9$,
(B) from 0.01 to 40% by mass of a powder having been subjected to a surface treatment with tridecafluoro octyltriethoxysilane,
(C) from 0.01 to 20% by mass of fine zinc oxide particles having a specific surface area of from 10 to 100 $m^2/g$, with the proviso that the component (B) is excluded from the component (C), and
(D) octyl para-methoxycinnamate,
wherein, a mass ratio of the component (A) to the component (D), (A)/(D), is from 0.5 to 10.

* * * * *